United States Patent [19]

Sedlacek et al.

[11] 4,157,383

[45] Jun. 5, 1979

[54] TANNED THROMBOCYTES

[75] Inventors: Hans-Harald Sedlacek; Roloff Johannsen; Fritz Seiler; Hermann Karges, all of Marburg, Fed. Rep. of Germany

[73] Assignee: Behringwerke Aktiengesellschaft, Marburg, Fed. Rep. of Germany

[21] Appl. No.: 732,134

[22] Filed: Oct. 13, 1976

[30] Foreign Application Priority Data

Oct. 15, 1975 [DE] Fed. Rep. of Germany ....... 2546166

[51] Int. Cl.² .................. A01N 1/02; G01N 1/00; G01N 31/00; G01N 33/16
[52] U.S. Cl. ................................. 424/3; 23/230 B; 252/408; 424/8; 424/12; 424/101
[58] Field of Search ................ 424/3, 8, 12, 101; 252/408; 23/230 B

[56] References Cited

U.S. PATENT DOCUMENTS

| | | | |
|---|---|---|---|
| 3,553,310 | 1/1971 | Csizmas | 424/2 |
| 3,753,357 | 8/1973 | Schwartz | 195/1.8 X |

OTHER PUBLICATIONS

Becht, J. of Immunology, vol. 101, 1968, pp. 18–22.
Silver, Chem. Abs., vol. 74, 1971, Ab. No. 945q.
Allain, Fed. Proc., vol. 33, Mar. 1974, p. 244, Ab. No. 233.
Karpatkin, Blood, The J. of Hematology, vol. 33, No. 6, Jun. 1969, pp. 795–812.
Sanbar, The Lancet, II, Oct. 28, 1967, pp. 917–919.
Silver, Pathology, vol. 2, 1970, pp. 199–207.
Behnke, Biol. Abs., vol. 47, 1966, Ab. No. 45218.
Gray, The Ency. of Microscopy and Microtech., Van Nostrand Reinhold Co., New York 1973, pp. 284–288.
Valone, Fed. Proc., vol. 33, No. 3, Mar. 1974, Ab. No. 231.

*Primary Examiner*—Anna P. Fagelson
*Attorney, Agent, or Firm*—Curtis, Morris & Safford

[57] ABSTRACT

The invention provides tanned thrombocytes, a process for preparing them and a diagnostic agent containing them to make evident antibodies of thrombocytes.

7 Claims, No Drawings

TANNED THROMBOCYTES

The invention relates to tanned thrombocytes, to a process for their preparation and to a diagnostic agent containing them to make evident antibodies of thrombocytes.

Thrombocytes are oval blood cells of 1 to 3 μm size with a metabolism of their own and a slightly basophilic protoplasm. Synonyms for thrombocytes are blood platelets and coagulum cells. Their activity in inducing the coagulation of blood is of physiological importance.

On the surface of the thrombocytes there are antigens which may lead to the formation of antibodies against these antigens. Thus the antigens of the thrombocytes are important for diagnostics. To make evident antibodies against antigens of thrombocytes, a thrombocyte composition freshly obtained from blood has hitherto been used.

The object of the invention is the stabilization of thrombocytes over rather a long period of time, without the antigens on the surface of the thrombocytes being considerably changed as to their immunological properties. This is achieved by treating thrombocytes with a tanning agent.

The invention relates to the tanned thrombocytes and to a process for their preparation. The invention further relates to agents for making evident antibodies of thrombocytes or antigens of thrombocytes containing the thrombocytes of the invention.

Tanning agents in the sense of the present invention are substances which are suitable and used in practice for converting animal skins into leather. Distinction is made between organic tanning agents of vegetal or synthetic origin and mineral tanning agents. The best known organic tanning agents of vegetal origin derive from gallic acid. There may be mentioned, for example, Turkish and the Chinese tannin. The synthetic organic tanning agents are mostly derivatives of mono- or polyvalent phenols. Other organic tanning agents are aldehydes and unsaturated fatty acids. Among the mineral tanning agents there may be mentioned the watersoluble 2- and 3-valent chromium salts, especially chromium(III)-chloride.

In the process for the preparation of tanned thrombocytes 5-sulfosalicylic acid or glutardialdehyde can be used with a particularly good result.

The concentration of the tanning agent solution to be used is expediently between 0.002 and 5% (w/v).

In the process, every composition of thrombocytes can be used in which the thrombocytes are enriched as compared with other particular blood constituents. There may be mentioned, for example, supernatant plasma enriched in thrombocytes obtained in known manner by the centrifugation of blood. It is expedient to wash this supernatant plasma before the reaction with the tanning agent by repeated centrifugation and resuspension in an isotonic solution optionally containing a metal-chelate forming agent such, as for example, ethylenediamino-tetra-acetic acid. The reaction of the thrombocytes with a tanning agent takes place in an isotonic aqueous medium containing a protective colloid.

Suitable protective colloids are the lyophilic colloids known to be particularly effective for aqueous systems, for example those colloids which are used for emulsion polymerization such as polyvinyl alcohol and polyacryl derivatives, as well as polyvinyl pyrrolidone, which has proved particularly suitable in the process of the present invention.

In a preferred variant of the process, the thrombocytes modified with a tanning agent are prepared as follows.

At first blood is rendered incoagulable in known manner with a suitable additive, for example with a substance forming a complex with calcium, or with a chelate-forming agent such as ethylene-diamino-tetra-acetic acid, or with another substance inhibiting coagulation, such as heparin. From this blood, the supernatant plasma enriched in thrombocytes is obtained by sedimentation or centrifugation at up to $300 \times g$. The thrombocytes are then collected by centrifugation at $100 \times g$ to $300 \times g$ in the sediment of centrifugation; after that the thrombocytes are resuspended and centrifuged in an isotonic physiologically compatible aqueous salt solution, for example a 0.9% sodium chloride solution which may contain 0.0001 mol to 0.0005 mol of a metal chelate-forming agent such as ethylenediamino-tetra-acetic acid. For the reaction the thrombocytes are used in a concentration of $10^5$ to $10^9$, preferably $3 \times 10^6$, per ml. The thrombocytes are counted with the aid of a counting chamber, for example according to Thoma. The dispersing agent is an aqueous buffer solution of a pH value of 6 to 8, which contains 0.01 to 5% of a lyophilic colloid, preferably polyvinyl pyrrolidone and, if desired, a chelate-forming agent in the above-mentioned concentration range.

The suspension is mixed with sulfo-salicylic acid up to a final concentration of 0.002 to 4%, preferably 1%, at 0° to 37° C., preferably 18° to 22° C., and left under these conditions for at least 15 minutes, preferably for about 1 hour. Then the thrombocytes are obtained by centrifugation at $100 \times g$ to $300 \times g$, resuspended with a neutral buffer solution, centrifuged again and resuspended finally in an aqueous solution preferably containing polyvinyl pyrrolidone. In this solution the tanned thrombocytes may be freeze-dried. The freeze-dried product may be resuspended homogeneously in water.

According to a further process preferably to be carried out, the thrombocytes are treated with glutardialdehyde in a final concentration of 0.001 to 4%, preferably 0.5%, under otherwise identical conditions as described for the sulfosalicylic acid. This composition, too, may be resuspended with a solution containing a protective colloid such as polyvinyl pyrrolidone and freeze-dried, if desired.

The tanned thrombocytes are globular and consistent and show a homogeneous structure as can be seen by an optical microscope. Seen with a naked eye or by optical microscope they do not show any spontaneous aggregation or an aggregation caused by unspecific antibodies.

Tanned thrombocytes, if suspended in solutions containing a protective colloid, can be stored at refrigerator temperature (about 4°) over several months without changing their properties. The freeze-dried compositions, which can be stored for a much longer time, show after resuspension the same properties they had before drying. The products prepared according to the invention are valuable agents to make evident antibodies of thrombocytes in serum or in serum compositions. For example the following test principles may be used.

Thrombocytes with known antigens on their surface are contacted with liquids containing antibodies against these known antigens. The immune complexes formed are made evident by the Coombs reaction, known to the expert, i.e. reacted with an antibody directed against the antibodies to be tested and marked in any known manner and made visible by the marking used.

Alternatively to the Coombs test, the immune complexes of thrombocyte antigens and -antibodies can be made evident by the equally known complement binding reaction. The test principle may also be used if the antigens on the thrombocytes are unknown and react with known antibodies directed against thrombocytes. The following test system may be used.

The sediment of about $1 \times 10^6$ thrombocytes stabilized according to the invention is diluted, optionally in several steps, with 0.1 ml of the liquid, for example, serum, to be tested for the presence of thrombocyte antibodies, covered with a layer and resuspended. After an incubation of about 30 minutes at about 20° C., the thrombocytes are washed three times, with a physiological salt solution containing if desired, 0.0001 mol to 0.0005 mol of a-metal chelate forming agent such as ethylene-diamino-tetra-acetic acid. Subsequently, the sediment of thrombocytes is covered with a layer of 0.1 ml of an antiserum containing antibodies against the thrombocyte antibodies to be tested, which first-mentioned antibodies are joined to a marking agent [for example a fluorescent substance such as fluorescein-isothiocyanate (FITC), or tetramethyl-rhodamineisothiocyanate (TRITC), or an enzyme such as peroxidase], and resuspended in a dilution which does no longer react (unspecifically) with the stabilized thrombocytes. After an incubation of 30 minutes at about 20° C., and after washing again three times, the sediment of thrombocytes is resuspended in 0.02 ml of a solution containing protein (for example albumin or the serum of a calf foetus). The suspension is spread out on a slide. After drying in air the composition is directly evaluated in a fluorescence microscope or it is subsequently subjected to one of the known cytochemical reactions for the marking enzyme and then evaluated by an optical microscope. If the liquid to be tested contains antibodies against thrombocytes, these particles are marked according to the method chosen and are detectable.

The following Example illustrates the invention.

EXAMPLE 100 ml of human blood, which has been mixed with 0.005 g of EDTA per ml while being taken from a patient, is centrifuged in a centrifuge at 1500 rpm (rotor diameter 21 cm). The supernatant, enriched in thrombocytes, is siphoned off and, the residue is rejected. The supernatant is then centrifuged at 1200 rpm and resuspended in a 0.9% sodium chloride solution containing 0.01 g of EDTA per 100 ml. Centrifugation and resuspension are repeated on the whole five times: in each case the supernatant is discarded and the sediment of thrombocytes is obtained.

Finally, the sediment of thrombocytes is resuspended in 25 ml of a solution buffered with phosphate with a pH value of 7.2 and which is mixed with 1% of polyvinyl pyrrolidone. The solution has the following composition:

| | |
|---|---|
| NaCl | 8 g |
| KCl | 0.2 g |
| $MgCl_2 \cdot 6H_2O$ | 0.1 g |
| $CaCl_2 \cdot 2H_2O$ | 0.132 g |
| $Na_2HPO_4 \cdot 12H_2O$ | 2.9 g |
| $KH_2PO_4$ | 0.2 g |
| Aqua bidest. ad | 1000 ml |

25 ml of a 2% 5-sulfo-salicylic acid solution dissolved in the above-mentioned phosphate buffer solution having a content of 1% by weight of polyvinyl pyrrolidone are added to the suspension of thrombocytes. The mixture is stirred for one hour at room temperature. The chemically modified thrombocytes are centrifuged at $180 \times g$ and are washed five times as earlier described with a phosphate buffer solution containing 0.01 g of EDTA per 100 ml. A total of 40 ml of washing liquid is obtained. Finally, the thrombocytes are obtained by centrifugation and resuspended in 30 ml of the phosphate buffer solution described, which contains 1 g of polyvinyl pyrrolidone per 100 ml.

In this form the suspension represents a diagnostically useful agent for the identification of antibodies of thrombocytes. To stabilize the suspension, an antimicrobially active agent, such as for example sodium thimerosal, may be added in a concentration of 0.001 g per 100 ml. The suspension obtained may be freeze-dried in known manner. Expediently, portions of 10 ml are filled into ampoules and freeze-dried.

In the same manner as in the preceding Example, tanned thrombocytes can be prepared with glutardialdehyde; instead of a 2% sulfo-salicylic acid a 1% glutardialdehyde solution is used.

What we claim is:

1. In a test method for the detection of antigens or antibodies of thrombocytes by the formation of immune complexes using thrombocytes as a diagnostic reagent, the improvement wherein said thrombocytes are tanned by suspending freshly-obtained thrombocytes in an isotonic, approximately neutral, aqueous solution containing a protective colloid and treating them with a tanning agent.

2. The method as in claim 1 wherein said tanning agent is sulfosalicylic acid or glutardialdehyde.

3. The method as in claim 1 wherein said protective colloid is a lyophilic colloid.

4. The method as in claim 1 wherein said aqueous solution additionally contains a chelating agent for metals.

5. The method of tanning thrombocytes which comprises suspending freshly-obtained thrombocytes in an isotonic, approximately neutral, aqueous solution containing a protective colloid and treating them with sulfosalicylic acid at a concentration from 0.002 to 4 percent, at a pH of 6 to 8, at a temperature of 0° C. to 37° C., and for a time from a few minutes up to several hours.

6. The method as in claim 5 wherein said protective colloid is a lyophilic colloid.

7. The method as in claim 6 wherein said lyophilic colloid is polyvinyl pyrrolidone and is present in said solution at a concentration from 0.01 to 5 percent.

* * * * *